US008163915B2

(12) United States Patent
Bunnelle

(10) Patent No.: US 8,163,915 B2
(45) Date of Patent: Apr. 24, 2012

(54) 4-SUBSTITUTED AZAADAMANTANE DERIVATIVES AND METHODS OF USE THEREOF

(75) Inventor: William H. Bunnelle, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 1040 days.

(21) Appl. No.: 12/052,061

(22) Filed: Mar. 20, 2008

(65) Prior Publication Data
US 2008/0255180 A1 Oct. 16, 2008

Related U.S. Application Data

(60) Provisional application No. 60/896,751, filed on Mar. 23, 2007.

(51) Int. Cl.
C07D 471/18 (2006.01)
(52) U.S. Cl. ......................................................... 546/94
(58) Field of Classification Search ........................ None
See application file for complete search history.

(56) References Cited

U.S. PATENT DOCUMENTS

| 4,816,453 | A | 3/1989 | Watts |
| 5,260,303 | A | 11/1993 | Becker et al. |
| 5,280,028 | A | 1/1994 | Flynn et al. |
| 5,399,562 | A | 3/1995 | Becker et al. |
| 5,434,151 | A | 7/1995 | Cai et al. |
| 5,512,579 | A | 4/1996 | Miyazawa et al. |
| 5,591,749 | A | 1/1997 | Becker et al. |
| 5,604,239 | A | 2/1997 | Becker et al. |
| 5,952,339 | A | 9/1999 | Bencherif et al. |

FOREIGN PATENT DOCUMENTS

| EP | 0227215 | 9/1987 |
| WO | 9215593 | 9/1992 |
| WO | 9400454 | 1/1994 |
| WO | WO-9951601 | 10/1999 |
| WO | WO-9951602 | 10/1999 |
| WO | WO-0011001 | 3/2000 |

OTHER PUBLICATIONS

Rautio et al., Prodrugs: Design and Clinical Applications, 7 Nat. Rev. Drug Dis., 255-70 (2008).*
F. Zaragoza Dorwald, Side Reactions in Organic Synthesis; A Guide to Successful Synthesis Design, Wiley-VCH, Weinheim, Preface, p. IX (2005).*
Adams, E., et al., Developmental Brain Research, 139: 175-187 (2002).
Adler, E., et al., Schizophrenia Bulletin, 24(2): 189-202 (1998).
Anderson, J., et al., Journal of Pharm. and Exp. Therap., 324(1): 179-187 (2008).
Balbani, A., et al., Expert. Opin. Ther. Pat., 17(3): 287-297 (2007).
Becker, D., et al., Synthesis: 1080-1082 (1992).
Bitner, R., et al., Neuroscience, 325.6 Abstract (2006).
Broad, L., et al., Drugs of the Future, 32(2): 161-170 (2007).
Bunnelle, W., et al., Expert Opin. Ther. Patents, 13(7): 1003-1021 (2003).
Cordero-Erausquin, M., et al., PNAS, 98(5): 2803-2807 (2001).
Couturier, S., et al., Neuron, 5: 847-856 (1990).
Dajas-Bailador, F., et al., Trends in Pharm. Sciences, 25(6): 317-324 (2004).
Decker, M., et al., Expert Opin. Investig. Drugs, 10(10): 1819-1830 (2001).
De Luca, V., et al., Acta Psychiatrica Scand., 114: 211-215 (2006).
Greene, T. W., et al., Protecting Groups in Chemical Synthesis (3rd ed), John Wiley & Sons, NY, Table of Contents (1999).
Falk, L., et al., Developmental Brain Research, 142: 151-160 (2003).
Flynn, D., et al., Bioorganic & Medicinal Chemistry Letters, 2(12): 1613-1618 (1992).
Alkondon, M., et al., Prog. Brain Res. 145: 109-120 (2004).
Friedman, J., et al., Society of Biol. Psych., 51: 349-357 (2002).
Geerts, H., Current Opinion in Invest. Drugs, 7(1): 60-69 (2006).
Gundisch, D., Expert Opin. Ther. Patents, 15(9): 1221-1239 (2005).
Gurwitz, D., Exp. Opin. Invest. Drugs, 8(6): 747-760 (1999).
Gotti, C., et al., Prog. Neurobiol., 74: 363-396 (2004).
Tsuneki, H., et al., J. Physiol., 547: 169-179 (2003).
Hogg, R., et al., Rev. Physiol. Biochem. Pharmacol., 147: 1-46 (2003).
Iriepa, I., et al., Journal of Molecular Structure, 509: 105-114 (1999).
Jonnala, R., et al., Journal of Neuroscience Research, 66: 565-572 (2001).
Keller, J., et al., Behay. Brain Research, 162: 143-152 (2005).
Kihara, T., et al., Journal of Biological Chemistry, 276: 13541-13546 (2001).
Leonard, S., et al., European Journal of Pharmacology, 393: 237-242 (2000).
Levin, E., J. Neurobiol., 53: 633-640 (2002).
Liu, Q., et al., PNAS, 98: 4734-4739 (2001).
Pabreza, L., et al., Molecular Pharmacology, 39: 9-12 (1991).
Paterson, D., et al., Progress in Neurobiology, 61: 75-111 (2000).
Prescott, D., Methods in Cell Biology, XIV: 33 et., Academic Press, New York, NY (1996).
Radek, R., et al., Psychopharmacology, 187: 47-55 (2006).
Rowley, M., et al., Journal of Medicinal Chemistry, 44(4): 477-501 (2001).
Sawa, A., et al., Molecular Medicine, pp. 3-9 (2003).
Shimohama, S., et al., Brain Research, 779: 359-363 (1988).
Stevens, K., Psychopharmacology, 136: 320-327 (1998).
Vincler, M., Expert Opin. Investig. Drugs, 14(10): 1191-1198 (2005).
Vincler, M., et al., Expert Opin. Ther. Targets, 11(7): 891-897 (2007).
Wilens, T., et al., Biol. Psychiatry, 59(11): 1065-1070 (2006).
Wilens, Timothy e. et al., Am J Psychiatry, 156(12): 1931-1937 (1999).
Rische, N. Chemische Berichte 118 (12):4949-4856 1985.
Alkondon, M. et al. Biochemical Pharmacology (75) 1134-1144 (2007).
PCT International Search Report, PCT/US2008/057647, mailing date Aug. 13, 2008.
EP Search Report for EP08/732558 dated Aug. 20, 2009.

* cited by examiner

Primary Examiner — Janet Andres
Assistant Examiner — Timothy R Rozof
(74) Attorney, Agent, or Firm — Lisa V. Mueller; Michael Best & Friedrich LLP

(57) ABSTRACT

The invention relates to compounds that are 4-substituted azaadamantane derivatives, compositions comprising such compounds, and methods of using such compounds and compositions.

10 Claims, No Drawings

4-SUBSTITUTED AZAADAMANTANE DERIVATIVES AND METHODS OF USE THEREOF

This application claims priority from U.S. Provisional Patent Application Ser. No. 60/896,751 filed Mar. 23, 2007, which is hereby incorporated by reference in its entirety.

BACKGROUND OF THE INVENTION

1. Technical Field

The invention relates to 4-substituted azaadamantane derivatives, compositions comprising such compounds, and methods of preventing or treating conditions and disorders using such compounds and compositions.

2. Description of Related Technology

Nicotinic acetylcholine receptors (nAChRs), belonging to the super family of ligand gated ion channels (LGIC), are widely distributed throughout the central nervous system (CNS) and the peripheral nervous system (PNS), and gate the flow of cations, controlled by acetylcholine (ACh). The nAChRs can be divided into nicotinic receptors of the muscular junction (NMJ) and neuronal nAChRs or neuronal nicotinic receptors (NNRs). The NNRs are understood to play an important role in regulating CNS function and the release of many neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of NNRs exist in the CNS and periphery. Each subtype has a different effect on regulating the overall physiological function.

Typically, NNRs are ion channels that are constructed from a pentameric assembly of subunit proteins. Sixteen subunits of nAChRs have been reported to date, which are identified as $\alpha 2$-$\alpha 10$, $\beta 1$-$\beta 4$, $\gamma$, $\delta$, and $\epsilon$. Of these subunits, nine subunits, $\alpha 2$ through $\alpha 7$ and $\beta 2$ through $\beta 4$, prominently exist in the mammalian brain. Multiple functionally distinct nAChR complexes also exist, for example five $\alpha 7$ subunits can form a receptor as a homomeric functional pentamer or combinations of different subunits can complex together as in the case of $\alpha 4\beta 2$ and $\alpha 3\beta 4$ receptors (see for example, Vincler, M., McIntosh, J. M., Targeting the $\alpha 9\alpha 10$ nicotinic acetylcholine receptor to treat severe pain, *Exp. Opin. Ther. Targets*, 2007, 11 (7): 891-897; Paterson, D. and Nordberg, A., Neuronal nicotinic receptors in the human brain, *Prog. Neurobiol.* 2000, 61: 75-111; Hogg, R. C., Raggenbass, M., Bertrand, D., Nicotinic acetylcholine receptors: from structure to brain function, *Rev. Physiol., Biochem. Pharmacol.*, 2003, 147: 1-46; Gotti, C., Clementi, F., Neuronal nicotinic receptors: from structure to pathology, *Prog. Neurobiol.*, 2004, 74: 363-396). These subunits provide for a great variety of homomeric and heteromeric combinations that account for the diverse receptor subtypes.

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain, and tobacco dependence (see for example, Keller, J. J., Keller, A. B., Bowers, B. J., Wehner, J. M., Performance of alpha7 nicotinic receptor null mutants is impaired in appetitive learning measured in a signaled nose poke task, *Behav. Brain Res.*, 2005, 162: 143-52; Gundish, D., Nicotinic acetylcholine receptor ligands as potential therapeutics, *Expert Opin. Ther. Patents*, 2005, 15 (9): 1221-1239; De Luca, V., Likhodi, O., Van Tol, H. H., Kennedy, J. L., Wong, A. H., Regulation of alpha7-nicotinic receptor subunit and alpha7-like gene expression in the prefrontal cortex of patients with bipolar disorder and schizophrenia, *Acta Psychiatr. Scand.*, 2006, 114: 211-5).

The homomeric $\alpha 7$ receptor is one of the most abundant nicotinic receptors, along with $\alpha 4\beta 2$ receptors, in the human brain, wherein it is heavily expressed in the hippocampus, cortex, thalamic nuclei, ventral tegmental area and substantia nigra (see for example, Broad, L. M., Sher, E., Astles, P. C., Zwart, R., O'Neill, M. J., Selective $\alpha 7$ nicotinic acetylcholine receptor ligands for the treatment of neuropsychiatric diseases, *Drugs of the Future*, 2007, 32(2): 161-170).

The role of $\alpha 7$ NNRs in neuronal signaling in the CNS also has been actively investigated (see for example, Couturier, S., Bertrand, D., Matter, J. M., Hernandez, M. C., Bertrand, S., Millar, N., Valera, S., Barkas, T., Ballivet, M., A neuronal nicotinic acetylcholine receptor subunit (alpha 7) is developmentally regulated and forms a homo-oligomeric channel blocked by alpha-BTX, *Neuron*, 1990, 5: 847-56). The $\alpha 7$ NNRs have been demonstrated to regulate interneuron excitability, modulate the release of excitatory and inhibitory neurotransmitters, and lead to neuroprotective effects in experimental in vitro models of cellular damage (see for example, Alkondon, M., Albuquerque, E. X., The nicotinic acetylcholine receptor subtypes and their function in the hippocampus and cerebral cortex, *Prog. Brain Res.*, 2004, 145: 109-20).

Biophysical studies have shown that ion channels comprised of $\alpha 7$ subunits, when expressed in heterologous expression systems, activate and desensitize rapidly, and furthermore, exhibit relatively higher calcium permeability compared to other NNR combinations (see for example, Dajas-Bailador, F., Wonnacott, S., Nicotinic acetylcholine receptors and the regulation of neuronal signaling, *Trends Pharmacol. Sci.*, 2004, 25: 317-24).

The NNR ligands have been also implicated in smoking cessation, weight control and as potential analgesics (see for example, Balbani, A. P. S., Montovani, J. C., Recent developments for smoking cessation and treatment of nicotine dependence, *Exp. Opin. Ther. Patents*, 2003, 13 (7): 287-297; Gurwitz, D., The therapeutic potential of nicotine and nicotinic agonists for weight control, *Exp. Opin. Invest. Drugs*, 1999, 8(6): 747-760; Vincler, M., Neuronal nicotinic receptors as targets for novel analgesics, *Exp. Opin. Invest. Drugs*, 2005, 14 (10): 1191-1198; Bunnelle, W. H., Decker, M. W., Neuronal nicotinic acetylcholine receptor ligands as potential analgesics, *Exp. Opin. Ther. Patents*, 2003, 13 (7): 1003-1021; Decker, M. W., Meyer, M. D., Sullivan, J. P., The therapeutic potential of nicotinic acetylcholine receptor agonists for pain control, *Exp. Opin. Invest. Drugs*, 2001, 10 (10): 1819-1830; Vincler, M., McIntosh, J. M., Targeting the $\alpha_9\alpha_{10}$ nicotinic acetylcholine receptor to treat severe pain, *Exp. Opin. Ther. Targets*, 2007, 11 (7): 891-897).

The $\alpha 7$ and $\alpha 4\beta 2$ NNRs have been shown to play a significant role in enhancing cognitive function, including aspects of learning, memory and attention (Levin, E. D., J. Neurobiol. 53: 633-640, 2002). For example, $\alpha 7$ NNRs have been linked to conditions and disorders related to attention deficit disorder, ADHD, AD, mild cognitive impairment, senile dementia, dementia associated with Lewy bodies, dementia associated with Down's syndrome, AIDS dementia, Pick's disease, as well as cognitive deficits associated with schizophrenia (CDS), among other systemic activities. The $\alpha 4\beta 2$ receptor subtype is implicated in attention, cognition, epilepsy, and pain control (Paterson, D. and Nordberg, A., Neuronal nicotinic receptors in the human brain, *Prog. Neurobiol.* 2000, 61: 75-111).

Certain compounds, like the plant alkaloid nicotine, interact with all known subtypes of the nAChRs, accounting for the profound physiological effects of this compound. Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems that interfere at therapeutic doses, and its addictive nature and acute toxicity are well-known. Accordingly, there is a need to identify subtype-selective compounds that evoke the beneficial effects of nicotine while eliminating or decreasing adverse effects.

The activity at the NNRs can be modified or regulated by the administration of subtype selective NNR ligands. The ligands can exhibit antagonist, agonist, or partial agonist properties and thus have potential in treatment of various cognitive disorders.

Although compounds that nonselectively demonstrate activity at a range of nicotinic receptor subtypes including the α4β2 and α7 NNRs are known, it would be beneficial to provide compounds that interact selectively with α7-containing neuronal NNRs, α4β2 NNRs, or both α7 and α4β2 NNRs compared to other subtypes.

SUMMARY OF THE INVENTION

The invention is directed to 4-substituted azaadamantane derivatives as well as compositions comprising such compounds, and method of using the same.

One aspect of the invention relates to a compound of formula (I)

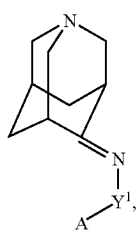

(I)

wherein
Y¹ is a bond, —N(R$^X$)—C(O)—, —O—, —N(R$^X$)—C(O)—N(R$^Y$)—, —O—C(O)—, or —N(R$^Z$)—;
wherein the —C(O) moiety of —N(R$^X$)—C(O)— and —O—C(O)— are attached to A of formula (I);
A is aryl, heteroaryl, heterocycle, cycloalkyl, cycloalkenyl, arylalkyl, heteroarylalkyl, heterocyclealkyl, cycloalkylalkyl, or cycloalkenylalkyl; and
R$^X$, R$^Y$, and R$^Z$, at each occurrence, are each independently hydrogen, alkyl, or haloalkyl;
or a pharmaceutically acceptable salt, amide, ester or prodrug thereof.

Another aspect of the invention relates to pharmaceutical compositions comprising compounds of the invention. Such compositions can be administered in accordance with a method of the invention, typically as part of a therapeutic regimen for treatment or prevention of conditions and disorders related to NNR activity, and more particularly α7 NNR activity, α4β2 NNR activity, or both α7 NNR activity and α4β2 NNR activity.

A further aspect of the invention relates to a method of modulating α7 NNR activity, α4β2 NNR activity, or both α7 NNR activity and α4β2 NNR activity. The method is useful for treating, preventing, or both treating and preventing conditions and disorders related to α7 NNR activity, α4β2 NNR activity, or both α7 NNR activity and α4β2 NNR activity in mammals. More particularly, the method is useful for conditions and disorders related to attention deficit disorder, ADHD, AD, Parkinson's disease, Tourette's syndrome, schizophrenia, cognitive deficits of schizophrenia (CDS), mild cognitive impairment, age-associated memory impairment (AAMI), senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, smoking cessation, ischemia, sepsis, wound healing, and other complications associated with diabetes, among other systemic and neuroimmunomodulatory activities.

Radiolabelled compounds useful for evaluating the binding affinity of substituted azaadamantane derivatives to α7 nicotinic acetylcholine receptors also are described herein.

The compounds, compositions comprising the compounds, and methods for treating or preventing conditions and disorders by administering the compounds are further described herein.

DETAILED DESCRIPTION OF THE INVENTION

Definition of Terms

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched, saturated hydrocarbon chain containing from 1 to 10 carbon atoms, including lower alkyl, $C_{1-6}$ alkyl and $C_{1-3}$ alkyl. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl, a bicyclic aryl, or a tricyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The tricyclic aryl is a bicyclic aryl fused to a monocyclic cycloalkyl, or a bicyclic aryl fused to a monocyclic cycloalkenyl, or a bicyclic aryl fused to a phenyl. Representative examples of tricyclic aryl ring include, but are not limited to, anthracene, phenanthrene, dihydroanthracenyl, fluorenyl, and tetrahydrophenanthrenyl. The aryl groups of the present invention can be unsubstituted or substituted and are attached to the parent molecular moiety through any carbon atom contained within the ring systems.

The term "arylalkyl" as used herein, means an aryl group, as defined herein, appended to the parent molecular moiety through an alkyl group, as defined herein. Representative examples of arylalkyl include, but are not limited to, benzyl (phenylmethyl), 2-phenylethyl, and 3-phenylpropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, or a tricyclic cycloalkyl. The monocyclic cycloalkyl is a saturated hydrocarbon ring system having three to eight carbon atoms, zero heteroatoms and zero double bonds. The monocyclic cycloalkyl can be attached to the parent molecular moiety through any substitutable atom contained within the monocyclic cycloalkyl. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, or three carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bridged bicyclic cycloalkyl in which two non-adjacent carbon atoms of the bicyclic ring system are linked by an alkylene bridge of between one and four carbon atoms. Representative examples of tricyclic-ring systems include, but are not limited to, tricyclo[3.3.1.0$^{3,7}$]nonane and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring systems.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, and cyclohexylmethyl.

The term "cycloalkenyl" or "cycloalkene" as used herein, means a monocyclic or a bicyclic hydrocarbon ring system. The monocyclic cycloalkenyl has four, five, six, seven or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms and each linking two non-adjacent carbon atoms of the ring. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted, and are attached to the parent molecular moiety through any substitutable atom contained within the ring systems.

The term "cycloalkenylalkyl" as used herein, means a cycloalkenyl group, as defined herein, appended to the parent molecular moiety through an alkyl group, as defined herein.

The term "ethylenedioxy" as used herein, means a —O—(CH$_2$)$_2$—O— group wherein the oxygen atoms of the ethylenedioxy group are attached to two adjacent carbon atoms of a phenyl or naphthyl moiety, forming a six membered ring with the two adjacent carbon atoms of the phenyl or naphthyl moiety that it is attached to.

The term "halo" or "halogen" as used herein, means —Cl, —Br, —I, or —F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, difluoromethyl, pentafluoroethyl, and 2-chloro-3-fluoropentyl.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or four nitrogen atoms; or one, two, or three nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]

pyridin-2-yl, thiazolo[5,4-d]pyrimidin-2-yl, thieno[2,3-c]pyridinyl, and 5,6,7,8-tetrahydroquinolin-5-yl. The monocyclic and bicyclic heteroaryl groups of the present invention can be substituted or unsubstituted, and are connected to the parent molecular moiety through any substitutable carbon atom or any substitutable nitrogen atom contained within the ring systems.

The term "heteroarylalkyl" as used herein, means a heteroaryl, as defined herein, appended to the parent molecular moiety through an alkyl group, as defined herein.

The term "heteroatom" as used herein, means a nitrogen, oxygen, or sulfur atom.

The term "heterocycle" or "heterocyclic" as used herein, means a monocyclic, a bicyclic, or a tricyclic heterocycle ring system, provided that the heterocycle is not 1,3-benzodioxolyl, 2,3-dihydro-1,4-benzodioxine, naphtho[2,3-d][1,3]dioxole, or 2,3-dihydronaphtho[2,3-b][1,4]dioxine. The monocyclic heterocycle is a three-, four-, five-, six-, or seven-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven-membered ring contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, tetrahydropyranyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge containing one, two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bridged bicyclic heterocycle in which two non adjacent atoms of the bicyclic ring are linked by an alkylene bridge consisting of one, two, three, or four carbon atoms. An example of a tricyclic heterocycle is azaadmantane such as 1-azatricyclo[3.3.1.1$^{3,7}$]decane. The monocyclic, bicyclic and tricyclic heterocycles are connected to the parent molecular moiety through any substitutable carbon or nitrogen atom contained within the ring systems, and can be unsubstituted or substituted.

The term "heterocyclealkyl" as used herein, means a heterocycle, as defined herein, appended to the parent molecular moiety through an alkyl group, as defined herein.

The term "methylenedioxy" as used herein, means a —O—(CH$_2$)—O— group wherein the oxygen atoms of the methylenedioxy group are attached to two adjacent carbon atoms of the phenyl or naphthyl ring, forming a five membered ring with the two adjacent carbon atoms of the phenyl or naphthyl moiety that it is attached to.

The term "oxo" as used herein, means a =O group.

The term "parenterally," as used herein, refers to modes of administration, including intravenous, intramuscular, intraperitoneal, intrasternal, subcutaneous, intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The term "pharmaceutically acceptable salts, esters and amides" as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base functional group with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, malate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate, and undecanoate.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The term "tautomer" as used herein means a proton shift from one atom of a compound to another atom of the same compound wherein two or more structurally distinct compounds are in equilibrium with each other.

The terms "unsubstituted or substituted" with reference to aryl, cycloalkyl, cycloalkenyl, heterocycle, or heteroaryl moieties of this invention, as a substituent, or as part of a substituent, each independently, as used herein mean unsubstituted or substituted with 1, 2, 3, 4, or 5 substituents as described hereinbelow, unless otherwise noted. The optional substituents are selected from the group consisting of alkyl, alkenyl, alkynyl, halogen, cyano, oxo, methylenedioxy, ethylenedioxy, -$G^1$, —$NO_2$, —$OR^{1a}$, —$OC(O)R^{1a}$, $OC(O)N(R^b)(R^a)$, —$SR^{1a}$, —$S(O)_2R^{2a}$, —$S(O)_2N(R^b)(R^{1a})$, —$C(O)R^{1a}$, —$C(O)OR$ $C(O)N(R^b)(R^{3a})$, —$N(R^b)(R^a)$, $N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m OR^{1a}$, $(CR^{4a}R^{5a})_m OC(O)R^{1a}$, $(CR^{4a}R^{5a})_m OC(O)N(R^b)(R^a)$, —$(CR^{4a}R^{5a})_m$—$SR^{1a}$, —$(CR^{4a}R^{5a})_m$—$S(O)_2R^{1a}$, $(CR^{4a}R^{5a})_m S(O)_2 N(R^b)(R^a)$, $(CR^{4a}R^{5a})_m$—$C(O)R^{1a}$, —$(CR^{4a}R^{5a})_m$—$C(O)OR^{1a}$, $(CR^{4a}R^{5a})_m C(O)N(R^b)(R^a)$, —$(CR^{4a}R^{5a})_m$—$N(R^b)(R^a)$, —$(CR^{4a}R^{5a})_m$—$N(R^a)C(O)R_{1a}$, $(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^a)$, —$(CR^{4a}R^{5a})_m$-$G^1$, cyanoalkyl, and haloalkyl; wherein $R^{1a}$ and $R^{3a}$, at each occurrence, are each independently hydrogen, alkyl, haloalkyl, $G^1$, or —$(CR^6R^7)_n$-$G^1$;

$R^{2a}$, at each occurrence, is independently alkyl, haloalkyl, $G^1$, or —$(CR^6R^7)_n$-$G^1$;

$R^{4a}$, $R^{5a}$, $R^6$, and $R^7$, at each occurrence, are each independently hydrogen, halogen, alkyl, or haloalkyl;

$R^a$ and $R^b$, at each occurrence, are each independently hydrogen, alkyl, or haloalkyl;

m and n, at each occurrence, are each independently 1, 2, 3, 4, or 5;

$G^1$ is aryl, heteroaryl, heterocycle, cycloalkyl, or cycloalkenyl, wherein each $G^1$ is independently unsubstituted or substituted with 1, 2, 3, 4 or 5 substituents selected from the group consisting of alkyl, alkenyl, alkynyl, halogen, cyano, oxo, methylenedioxy, ethylenedioxy, —$NO_2$, —$OR^{1b}$, —$OC(O)R^{1b}$, —$OC(O)N(R^b)(R^b)$, —$SR_{1b}$, —$S(O)_2R^{2b}$, —$S(O)_2N(R^b)(R^b)$, —$C(O)R^{1b}$, —$C(O)OR^{1b}$, —$C(O)N(R^b)(R^b)$, —$N(R^b)(R^{3b})$, —$N(R^a)C(O)R^{1b}$, —$N(R^a)S(O)_2R^{2b}$, —$N(R^a)C(O)O(R^{1b})$, —$N(R^a)C(O)N(R^b)(R^{3b})$, $(CR^{4b}R^{5b})_m$—$NO_2$, —$(CR^{4b}R^{5b})_m$—$OR^{1b}$, —$(CR^{4b}R^{5b})_m OC(O)R^{1b}$, —$(CR^{4b}R^{5b})_m OC(O)N(R^b)(R^{3b})$, —$(CR^{4b}R^{5b})_m$—$SR^{1b}$, —$(CR^{4b}R^{5b})_m S(O)_2R^{2b}$, —$(CR^{4b}R^{5b})_m S(O)_2 N(R^b)(R^{3b})$, —$(CR^{4b}R^{5b})_m$—$C(O)R^{1b}$, —$(CR^{4b}R^{5b})_m$—$C(O)OR^{1b}$, —$(CR^{4b}R^{5b})_m C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)S(O)_2R^{2b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, cyanoalkyl, and haloalkyl;

$R^{1b}$ and $R^{3b}$, at each occurrence, are each independently hydrogen, alkyl, or haloalkyl;

$R^{2b}$, at each occurrence, is independently alkyl or haloalkyl; and $R^{4b}$ and $R^{5b}$, at each occurrence, are each independently hydrogen, halogen, alkyl, or haloalkyl.

Compounds of the Invention

One aspect of the invention relates to a compound of formula (I)

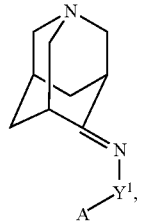

(I)

wherein $Y^1$ is a bond, —$N(R^X)$—$C(O)$—, —$O$—, —$N(R^X)$—$C(O)$—$N(R^Y)$—, —$O$—$C(O)$—, or —$N(R^Z)$—;

A is unsubstituted or substituted aryl, heteroaryl, heterocycle, cycloalkyl, cycloalkenyl, arylalkyl, heteroarylalkyl, heterocyclealkyl, cycloalkylalkyl, or cycloalkenylalkyl; and $R^X$, $R^Y$, and $R^Z$, at each occurrence, are each independently hydrogen, alkyl, or haloalkyl;

or a pharmaceutically acceptable salt, amide or prodrug thereof.

In another embodiment, the invention relates to compounds of formula (I), wherein $Y^1$ is attached to A of formula (I) through —C(O) moiety, when $Y^1$ is —$N(R^X)$—C(O)— or —O—C(O)—, or pharmaceutically acceptable salts, amides and prodrugs thereof.

In one embodiment, the invention relates to compounds of formula (I), wherein $Y^1$ is —$N(R^X)$—C(O)— and $R^X$ is hydrogen, alkyl, or haloalkyl, or pharmaceutically acceptable salts, amides and prodrugs thereof. One particular example of $R^X$ is hydrogen.

In another embodiment, the invention relates to compounds of formula (I), wherein $Y^1$ is —O—. In yet another embodiment, $Y^1$ is —$N(R^X)$—C(O)—$N(R^Y)$—, and $R^X$ and $R^Y$ are each independently hydrogen, alkyl, or haloalkyl, or pharmaceutically acceptable salts, amides and prodrugs thereof. Particular examples of $R^X$ and $R^Y$ are hydrogen.

In another embodiment, the invention relates to compounds of formula (I), wherein $Y^1$ is —O—C(O)—, or pharmaceutically acceptable salts, amides and prodrugs thereof.

In another embodiment, the invention relates to compounds of formula (I), wherein $Y^1$ is —$N(R^Z)$— and $R^Z$ is hydrogen, alkyl, or haloalkyl, or pharmaceutically acceptable salts, amides and prodrugs thereof. One particular example of $R^Z$ is hydrogen.

In one embodiment, the invention relates to compounds of formula (I), wherein A is aryl (for example, phenyl or naphthyl) or heteroaryl (for example, indolyl or pyridinyl), each of which is independently unsubstituted or substituted, or pharmaceutically acceptable salts, amides and prodrugs thereof.

In another embodiment, the invention relates to compounds of formula (I), wherein A is arylalkyl (for example, benzyl or naphthylmethyl) or heteroarylalkyl (for example, pyridinylmethyl or indolylmethyl) wherein the aryl moiety of the arylalkyl and the heteroaryl moiety of the heteroarylalkyl are each independently unsubstituted or substituted, or pharmaceutically acceptable salts, amides or prodrugs thereof.

One aspect of the invention relates to compounds of formula (I), wherein $Y^1$ is —$N(R^X)$—C(O)—, A is aryl or heteroaryl, and $R^X$ is hydrogen, alkyl, or haloalkyl, or pharmaceutically acceptable salts, amides and prodrugs thereof. Of this group of compounds, examples of a subgroup include those wherein $R^X$ is hydrogen.

Another aspect of the invention relates to compounds of formula (I), wherein y' is —N($R^X$)—C(O)—, A is arylalkyl or heteroarylalkyl, and $R^X$ is hydrogen, alkyl, or haloalkyl, or pharmaceutically acceptable salts, amidesand prodrugs thereof. Of this group of compounds, examples of a subgroup include those wherein $R^X$ is hydrogen.

Yet another aspect of the invention relates to compounds of formula (I), wherein $Y^1$ is —O—, A is aryl or heteroaryl, or pharmaceutically acceptable salts, amidesand prodrugs thereof.

Yet another aspect of the invention relates to compounds of formula (I), wherein $Y^1$ is —O—, A is arylalkyl or heteroarylalkyl, or pharmaceutically acceptable salts, amidesand prodrugs thereof.

A further aspect of the invention relates to compounds of formula (I), wherein $Y^1$ is —N($R^X$)—C(O)—N($R^Y$)—, A is aryl or heteroaryl, and $R^X$ and $R^Y$ are each independently hydrogen, alkyl, or haloalkyl, or pharmaceutically acceptable salts, amidesand prodrugs thereof. Of this group of compounds, examples of a subgroup include those wherein $R^X$ and $R^Y$ are hydrogen.

Yet another aspect of the invention relates to compounds of formula (I), wherein $Y^1$ is —N($R^X$)—C(O)—N($R^Y$)—, A is arylalkyl or heteroarylalkyl, and $R^X$ and $R^Y$ are each independently hydrogen, alkyl, or haloalkyl, or pharmaceutically acceptable salts, amides and prodrugs thereof. Of this group of compounds, examples of a subgroup include those wherein $R^X$ and $R^Y$ are hydrogen.

Yet another aspect of the invention relates to compounds of formula (I), wherein $Y^1$ is —N($R^Z$)—, A is aryl or heteroaryl, and $R^Z$ is hydrogen, alkyl, or haloalkyl, or pharmaceutically acceptable salts, amides and prodrugs thereof. Of this group of compounds, examples of a subgroup include those wherein $R^Z$ is hydrogen.

Yet another aspect of the invention relates to compounds of formula (I), wherein $Y^1$ is —N($R^Z$)—, A is arylalkyl or heteroarylalkyl, and $R^Z$ is hydrogen, alkyl, or haloalkyl, or pharmaceutically acceptable salts, amides, esters, and prodrugs thereof. Of this group of compounds, examples of a subgroup include those wherein $R^Z$ is hydrogen.

Exemplary compounds of formula (I) include, but are not limited to:

1-azatricyclo[3.3.1.1$^{3,7}$]decan-4-one O-2-naphthyloxime;
1-azatricyclo[3.3.1.1$^{3,7}$]decan-4-one O-(pentafluorobenzyl) oxime;
1-azatricyclo[3.3.1.1$^{3,7}$]decan-4-one O-(4-chlorophenyl) oxime;
1-azatricyclo[3.3.1.1$^{3,7}$]decan-4-one O-(6-chloropyridin-3-yl)oxime;
N'-1-azatricyclo [3.3.1.1$^{3,7}$]dec-4-ylidene-1H-indole-3-carbohydrazide; and
1-azatricyclo[3.3.1.1$^{3,7}$]decan-4-one O-benzyloxime.

or pharmaceutically acceptable salts, amides or prodrugs thereof.

Compounds disclosed herein may contain asymmetrically substituted carbon or sulfur atoms, and accordingly may exist in, and be isolated as, single stereoisomers (e.g. single enantiomer or single diastereomer), mixtures of stereoisomers (e.g. any mixture of enantiomers or diastereomers) or racemic mixtures thereof. Individual optically-active forms of the compounds can be prepared for example, by synthesis from optically-active starting materials, by chiral synthesis, by enzymatic resolution, by biotransformation, or by chromatographic separation. It is to be understood that the present invention encompasses any racemic, optically-active, stereoisomeric form, or mixtures of various proportions thereof, which form possesses properties useful in the modulation of NNRs activity, particularly α7NNRs, α4β2, or both α7 and α4β2. Where the stereochemistry of the chiral centers present in the chemical structures illustrated herein is not specified, the chemical structure is intended to encompass compounds containing either configuration of each chiral center, and mixtures thereof.

Geometric isomers can exist in the present compounds. The invention contemplates the various geometric isomers and mixtures thereof resulting from the disposition of substituents around a carbon-carbon double bond, a carbon nitrogen double bond, a cycloalkyl group, or a heterocycloalkyl group. Substituents around a carbon-carbon or carbon-nitrogen double bond are designated as being of Z or E configuration and substituents around a cycloalkyl or heterocycle are designated as being of cis or trans configuration.

For example, compounds of the invention can exist in the forms represented by formulas (Ia) and (Ib):

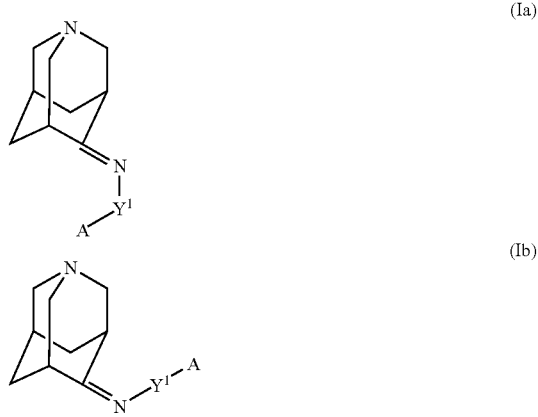

One skilled in the art will recognize that formulas (Ia) and (Ib) represent enantiomers when a chiral center is not present on —$Y^1$-A. However, when —$Y^1$-A does contain one or more asymmetric centers, the geometric isomers about the C=N bond will be diastereomers.

It is to be understood that formula (I) includes formula (Ia), (Ib), or mixtures of both in various ratios. Thus, compounds of formula (Ia), (Ib), or mixtures of both in various proportions are useful in modulating the effects of NNRs, and more particularly α7 NNRs, α4β2 NNRs, or both α7 and α4β2 NNRs.

It is to be understood that compounds disclosed herein may exhibit the phenomenon of tautomerism.

The compounds within this specification may be represented only by one of the possible tautomeric, geometric or stereoisomeric forms in naming of the compounds or formulae drawings. However, it is to be understood that the invention encompasses any tautomeric, geometric or stereoisomeric forms, and mixtures thereof, and is not to be limited merely to any one tautomeric, geometric or stereoisomeric form utilized within the naming of the compounds or formulae drawings.

Amides, Esters and Prodrugs

Prodrugs are pharmacologically inactive derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated herein in its entirety by reference.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

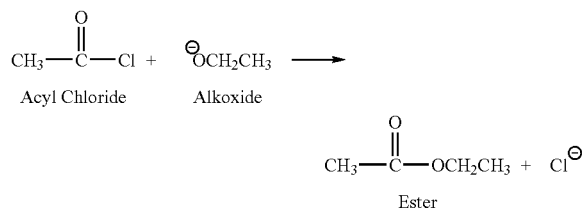

Scheme 1

Amides can be prepared from substrates of formula (I) containing either an amino group or a carboxy group in similar fashion. Esters can also react with amines or ammonia to form amides.

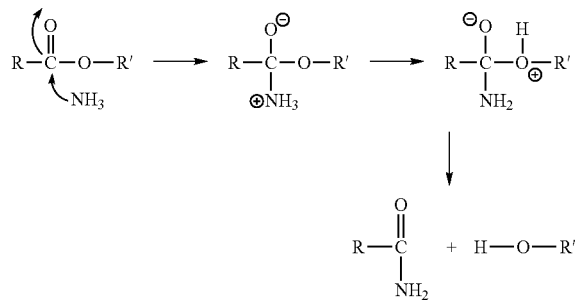

Scheme 2

Another way to make amides from compounds of formula (I) is to heat carboxylic acids and amines together.

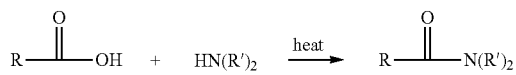

Scheme 3

In Schemes 2 and 3, R and R' are independently substrates of formula (I), alkyl or hydrogen. Various embodiments of the invention of formula (I) that are substrates for prodrugs, amides and esters include, but are not limited to, Example 5.

Compositions of the Invention

The invention also provides pharmaceutical compositions comprising of compounds of the invention, or pharmaceutically acceptable salts, amides, esters, prodrugs, or salts of prodrugs thereof, formulated together with one or more pharmaceutically acceptable carriers.

The compounds identified by the methods described hereinabove may be administered as the sole pharmaceutical agent or in combination with one or more other pharmaceutical agents where the combination causes no unacceptable adverse effects. For example, the compounds of this invention can be combined with an atypical antipsychotic. Specific examples of suitable atypical antipsychotics include, but are not limited to, clozapine, risperidone, olanzapine, quietapine, ziprasidone, zotepine, iloperidone, and the like. Thus, the present invention also includes pharmaceutical compositions which are comprised of therapeutically effective amount of compounds identified by the methods described herein, or pharmaceutically acceptable salts, prodrugs or salts of prodrugs thereof, one or more pharmaceutical agents as disclosed hereinabove, and one or more pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The pharmaceutical compositions can be formulated in solid, semi-solid or liquid form, for oral administration.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that releases the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as benzenesulfonic acid, citric acid, gluconic acid, maleic acid, oxalic acid, and succinic acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, and piperazine.

Compounds of the invention may exist as prodrugs. Prodrugs of the invention can be rapidly transformed in vivo to a parent compound of the invention, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof may be converted through in vivo biotransformation into compounds of formula (I).

Methods of the Invention

Compounds and compositions of the invention are useful for modulating the effects of NNRs, and more particularly $\alpha 7$ NNRs, $\alpha 4\beta 2$ NNRs, or both $\alpha 7$ and $\alpha 4\beta 2$ NNRs. In particular, the compounds and compositions of the invention can be used for treating or preventing disorders modulated by $\alpha 7$ NNRs, or $\alpha 4\beta 2$ NNRs, or both $\alpha 7$ and $\alpha 4\beta 2$ NNRs. Typically, such disorders can be ameliorated by selectively modulating the $\alpha 7$ NNRs, $\alpha 4\beta 2$ NNRs, or both $\alpha 7$ and $\alpha 4\beta 2$ NNRs in a mammal, preferably by administering a compound or composition of the invention, either alone or in combination with one or more additional pharmaceutical agents, for example, as part of a therapeutic regimen.

Compounds for the method of the invention, including but not limited to those specified in the examples or otherwise specifically named, can modulate, and often possess an affinity for, NNRs, and more particularly $\alpha 7$ NNRs, $\alpha 4\beta 2$ NNRs, or both $\alpha 7$ and $\alpha 4\beta 2$ NNRs. As $\alpha 7$ NNRs, $\alpha 4\beta 2$ NNRs, or both $\alpha 7$ and $\alpha 4\beta 2$ NNRs ligands, the compounds of the invention can be useful for the treatment or prevention of a number of $\alpha 7$ NNR, $\alpha 4\beta 2$ NNR, or both $\alpha 7$ and $\alpha 4\beta 2$ NNR mediated diseases or conditions.

Specific examples of compounds that can be useful for the treatment or prevention of $\alpha 7$, $\alpha 4\beta 2$, or both $\alpha 7$ and $\alpha 4\beta 2$ NNRs mediated diseases or conditions include, but are not limited to, compounds described in the Compounds of the Invention and also in the Examples.

Methods for preparing compounds useful in the method of the invention also can be found in Iriepa, I, et al. *J. Molec. Struct.* 1999, 509, 105; Flynn, D. L., et al. *Bioorganic & Medicinal Chemistry Letters,* 1992, 2, 1613; U.S. Pat. No. 4,816,453; WO 94/00454; U.S. Pat. Nos. 5,280,028; 5,399, 562; WO 92/15593; U.S. Pat. Nos. 5,260,303; 5,591,749; 5,434,151; and 5,604,239.

For example, $\alpha 7$ NNRs have been shown to play a significant role in enhancing cognitive function, including aspects of learning, memory and attention (Levin, E. D., J. Neurobiol. 53: 633-640, 2002). As such, $\alpha 7$ ligands are suitable for the treatment of conditions and disorders related to memory and/or cognition including, for example, attention deficit disorder, ADHD, AD, mild cognitive impairment, senile dementia, AIDS dementia, Pick's disease, dementia associated with Lewy bodies, and dementia associated with Down's syndrome, as well as CDS.

In addition, $\alpha 7$-containing NNRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of $\alpha 7$ NNRs by $\beta$-amyloid peptides linked to Alzheimer's disease has been implicated as a key factor in development of the cognitive deficits associated with the disease (Liu, Q.-S., Kawai, H., Berg, D. K., Proc. Natl. Acad. Sci. USA 98: 4734-4739, 2001). $\alpha 7$ selective ligands can influence neuroprotective pathways leading to decreased phosphorylation of the tau protein, whose hyperphosphorylation is required for neurofibrillary tangle formation in various tau related pathologies such as Alzheimer's disease and various other dementias (Bitner et al., Soc. Neuroscience, 2006 abst 325.6). The activation of $\alpha 7$ NNRs has been shown to block this neurotoxicity (Kihara, T. et al., J. Biol. Chem. 276: 13541-13546, 2001). As such, selective ligands that enhance $\alpha 7$ activity can counter the deficits of Alzheimer's and other neurodegenerative diseases.

$\alpha 7$ NNRs also have been implicated in aspects of neurodevelopment, for example neurogenesis of the brain (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, $\alpha 7$ NNRs can be useful in preventing or treating conditions or disorders associated with impaired neurodevelopment, for example schizophrenia. (Sawa A., Mol. Med. 9:3-9, 2003).

Several compounds with high affinity for $\alpha 4\beta 2$ NNRs have been shown to improve attentive and cognitive performance in preclinical models that are relevant to attention-deficit/hyperactivity disorder (ADHD), a disease characterized by core symptoms of hyperactivity, inattentiveness, and impulsivity. For example, ABT-418, a full agonist at $\alpha 4\beta 2$ NNRs, is efficacious in a variety of preclinical cognition models. ABT-418 administered transdermally, was shown in a controlled clinical trial in 32 adults to be effective in treating ADHD in general, and attentional/cognitive deficits in particular (Wilens, T. E.; Biederman, J.; Spencer, T. J.; Bostic, J.; Prince, J.; Monuteaux, M. C.; Soriano, J.; Fince, C.; Abrams, A.; Rater, M.; Polisner, D., *The American Journal of Psychiatry* (1999)156(12), 1931-1937). Likewise, ABT-418 showed a signal of efficacy in a pilot Alzheimer's disease trial. ABT-089, a $\alpha 4\beta 2$ selective partial agonist, has been shown in rodent and primate animal models to improve attention, learning, and memory deficits. ABT-089 and another $\alpha 4\beta 2$ agonist, ispronicline have shown efficacy in a pilot clinical trials (Wilens, T. E.; Verlinden, M. H.; Adler, L. A.; Wozniak, P. J.; West, S. A. *Biological Psychiatry* (2006), 59(11), 1065-1070. Geerts, H., *Curr. Opin. Invest. Drugs* (2006), 7(1), 60-69). In addition to cognition, compounds that interact with $\alpha 4\beta 2$ NNRs such as ABT-594 and others are also efficacious in preclinical and clinical models of pain. As such, ligands that modulate both $\alpha 7$ and $\alpha 4\beta 2$ activity can have broader spectrum of therapeutic efficacy in disease states such as those involving cognitive and attentive deficits, pain, neurodegenerative diseases and others.

Schizophrenia is a complex disease that is characterized by abnormalities in perception, cognition, and emotions. Significant evidence implicates the involvement of $\alpha 7$ NNRs in this disease, including a measured deficit of these receptors in post-mortem patients (Sawa A., *Mol. Med.* 9:3-9, 2003; Leonard, S. *Eur. J. Pharmacol.* 393: 237-242, 2000). Deficits in sensory processing (gating) are one of the hallmarks of schizophrenia. These deficits can be normalized by nicotinic ligands that operate at the $\alpha 7$ NNR (Adler L. E. et al., *Schizophrenia Bull.* 24: 189-202, 1998; Stevens, K. E. et al., *Psychopharmacology* 136: 320-327, 1998). More recent studies have shown that $\alpha 4\beta 2$ nicotinic receptor stimulation also contributes to the effects of nicotine in the DBA/2 mouse model of sensory gating (Radek et al., *Psychopharmacology* (Berl). 2006 187:47-55). Thus, $\alpha 7$ and $\alpha 7/\alpha 4\beta 2$ ligands demonstrate potential in the treatment schizophrenia.

A population of $\alpha 7$ or $\alpha 4\beta 2$ NNRs in the spinal cord modulate neurotransmission that has been associated with the pain-relieving effects of nicotinic compounds (Cordero-Erausquin, M. and Changeux, J.-P., *Proc. Natl. Acad. Sci. USA* 98:2803-2807, 2001). The $\alpha 7$ NNR or and $\alpha 7/\alpha 4\beta 2$ ligands demonstrate therapeutic potential for the treatment of pain states, including acute pain, post-surgical pain, as well as chronic pain states including inflammatory pain and neuropathic pain.

Compounds of the invention are particularly useful for treating and preventing a condition or disorder affecting memory, cognition, neurodegeneration, neurodevelopment, and schizophrenia.

Cognitive impairment associated with schizophrenia (CDS) often limits the ability of patients to function normally, a symptom not adequately treated by commonly available treatments, for example, treatment with an atypical antipsychotic. (Rowley, M. et al., *J. Med. Chem.* 44: 477-501, 2001). Such cognitive deficit has been linked to dysfunction of the nicotinic cholinergic system, in particular with decreased activity at $\alpha 7$ receptors. (Friedman, J. I. et al., *Biol. Psychiatry*, 51: 349-357, 2002). Thus, activators of (7 receptors can provide useful treatment for enhancing cognitive function in schizophrenic patients who are being treated with atypical antipsychotics. Accordingly, the combination of an $\alpha 7$ NNR ligand and one or more atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Compounds of the invention may be administered alone or in combination (i.e. co-administered) with one or more additional pharmaceutical agents. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salts thereof. Compounds of the invention can also be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) wherein the groups $R^X$, $R^Y$, $R^Z$, and A have the meanings as set forth in the Summary of the Invention section unless otherwise noted, is exemplified in Schemes 4 and 5.

As used in the descriptions of the schemes and the examples, certain abbreviations are intended to have the following meanings: BOC for tert-butoxycarbonyl; BSS for balanced salt solution; HPLC for high pressure liquid chromatography; and Tris for tris(hydroxymethyl)aminomethane.

Compounds of general formula (I) can be prepared from 1-azatricyclo[3.3.1.1$^{3,7}$]decan-4-one using general procedures as outlined in Scheme 4.

Hydroxyamine ethers of formula (1), can be treated with 1-azatricyclo[3.3.1.1$^{3,7}$]decan-4-one (prepared as reported in Becker, D. P. and Flynn, D. L. Synthesis 1992, 1080-1082), to provide oxime ethers of formula (2). Conversion of 1-azatricyclo[3.3.1.1$^{3,7}$]decan-4-one to compounds of formula (4) can be achieved by reaction with hydrazides of formula (3). Both reactions are generally conducted under acidic conditions wherein the acid is added prior to the reaction or is present as an acid salt of (1) or (3), at a temperature range from about room temperature to about 80° C., in a solvent such as ethanol.

1-azatricyclo[3.3.1.1$^{3,7}$]decan-4-one can also be treated with amines of formula (4a), hydrazines of formula (4c) and semicarbazides of formula (4e) to provide compounds of formula (4b), (4d) and (4f) respectively, using procedures similar to those known in the literatures. Many of the amines of formula (4a) and hydrazines of formula (4c) are commercially available. Semicarbazides of formula (4e) can be prepared from isocyanates or hydrazines using procedures analogous to those described in J. Med. Chem. (2003) 46, 1493-1503.

Scheme 4

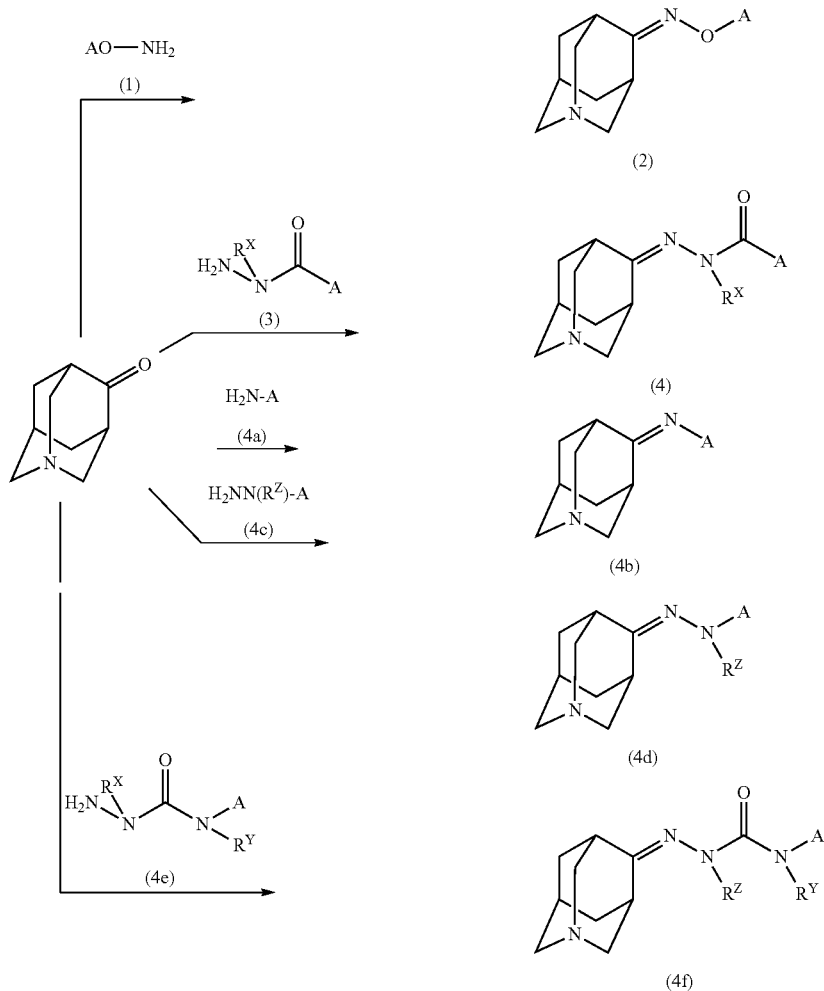

Hydroxyamine ethers of formula (1) can be prepared using general procedures as illustrated in Scheme 5.

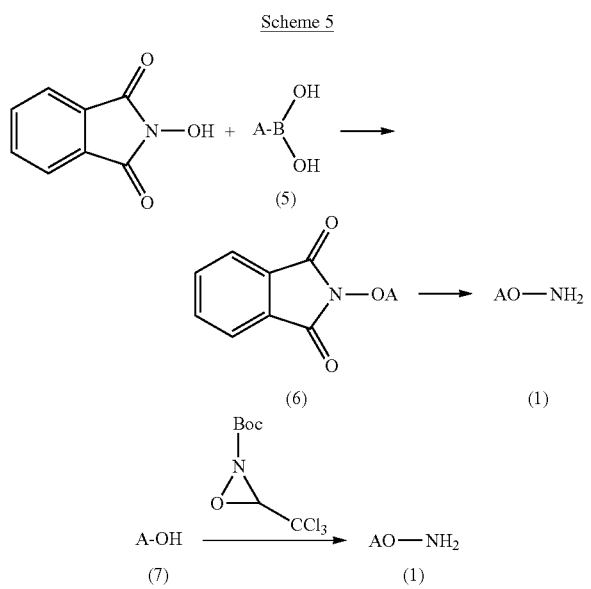

Boronic acids of formula (5) when treated with N-hydroxyphthalimide utilizing conditions known to those skilled in the art, for example, via a copper mediated cross-coupling reaction conditions, provide compounds of formula (6). For example, boronic acids of formula (5) and hydroxyphthalimide in the presence of a copper salt and a base and in a solvent such as but not limited to dichloromethane or 1,2-dichloroethane or mixtures thereof, optionally in the presence of molecular sieves, can be converted to compounds of formula (6). The reaction is generally carried out at temperature ranging from about room temperature to about 150° C. Examples of copper salts include, but are not limited to, $Cu(CO_2CH_3)_2$, CuCl, and $CuBr.S(CH_3)_2$. Examples of bases include, but are not limited to pyridine, 4-dimethylaminopyridine, and triethylamine.

Treatment of (6) with hydrazine monohydrate in solvents such as but not limited to chloroform, methanol or mixtures thereof provides hydroxyamine ethers (1).

Alternatively, hydroxyamine ethers of formula (1) can be obtained from alcohols of formula (7) as described in *Chem. Commun.*, 2000, 975-976, by treatment with a base followed by tert-butyl 2-(trichloromethyl)-1,2-oxaziridine-3-carboxylate. Examples of suitable bases for such conversion include, but are not limited to, sodium hydride, n-butyllithium, and the like. The reaction is generally carried out below ambient temperature and in a solvent such as, but not limited to, ether, tetrahydrofuran, or mixtures thereof.

Hydrazides of formula (3) can be prepared using methodologies analogous to those known in the art. For example, by acylating acid chlorides of formula AC(O)Cl (prepared from the corresponding acids) with appropriate hydrazines of formula $NH(R^X)NH_2$.

It will be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the convention manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The compounds of the invention and processes for making compounds for the method of the invention will be better understood by reference to the following examples, which are intended as an illustration of and not a limitation upon the scope of the invention.

EXAMPLES

Example 1

1-azatricyclo[3.3.1.1$^{3,7}$]decan-4-one O-2-naphthyloxime

Example 1A 2-(2-naphthyloxy)-1H-isoindole-1,3(2H)-dione

The title compound was prepared as described in Example 3A, substituting 2-naphthylboronic acid for 4-chlorophenyboronic acid.

Example 1B

O-(2-naphthyl)hydroxylamine

The title compound was prepared as described in Example 3B, substituting Example 1A for Example 3A. $^1$H NMR (300 MHz, CD$_3$OD) δ 7.16 (dd, J=9, 3 Hz, 1 H), 7.24-7.31 (m, 1 H), 7.35-7.42 (m, 1 H), 7.55 (d, J=2 Hz, 1 H), 7.67-7.76 (m, 3 H); MS (DCI/NH$_3$) m/z 160 (M+H).

Example IC 1-azatricyclo[3.3.1.1$^{3,7}$]decan-4-one O-2-naphtyloxime 1-azatricyclo[3.3.1.1$^{3,7}$]decan-4-one (74 mg, 0.49 mmol) (prepared as reported in: Becker, D. P. and Flynn, D. L. Synthesis 1992, 1080-1082) and Example IB (78 mg, 0.48 mmol) were combined in a test tube. Ethanol (4 mL) was added, followed by concentrated HCl (0.1 mL). The mixture was heated to boiling for 30 seconds, and the resulting solution was allowed to cool to room temperature overnight. The mixture was concentrated under vacuum, and the residue was crystallized from ethanol (1 mL) and ethyl acetate (5 mL) to provide the title compound as a hydrochloride salt. $^1$H NMR (300 MHz, CD$_3$OD) δ 2.18 (t, J=13 Hz, 2 H), 2.34-2.49 (m, 3 H), 3.10-3.16 (m, 1 H), 3.65-3.76 (m, 4 H), 3.77-3.84 (m, 1 H), 3.83-3.90 (m, 1 H), 4.10 (s, 1 H), 7.30-7.36 (m, 2 H), 7.40-7.48 (m, 1H), 7.64 (d, J=2 Hz, 1 H), 7.73-7.85 ppm (m, 3 H); MS (DCI/NH$_3$) m/z 293 (M+H)$^+$.

Example 2

1-azatricyclo[3.3.1.1$^{3,7}$]decan-4-one O-(pentafluorobenzyl)oxime

Solid O-(perfluorobenzyl)hydroxylamine HCl (167 mg, 0.669 mmol, Aldrich Chemical Co.) was added to a warm solution of 1-azatricyclo[3.3.1.1$^{3,7}$]decan-4-one (102 mg, 0.675 mmol) (prepared as reported in: Becker, D. P. and Flynn, D. L. Synthesis 1992, 1080-1082) in ethanol (1 mL). The mixture was swirled with warming to dissolve all solids. The nearly colorless solution was allowed to cool to room temperature overnight. The solvent was removed under vacuum, and the residue was crystallized from 10% ethanol in ethyl acetate (3 mL) to provide the title compound as hydrochloride salt. $^1$H NMR (300 MHz, CD$_3$OD) δ 1.87-2.06 (m, 2 H), 2.22 (q, J=3 Hz, 1 H), 2.24-2.37 (m, 2 H), 2.83 (s, 1H), 3.30, (m, 1H), 3.43-3.57 (m, 2 H), 3.64 (s, 2 H), 3.66-3.78 (m, 2 H), 5.15-5.24 ppm (m, 2 H); MS (DCI/NH$_3$) m/z 347 (M+H)$^+$; Anal. C$_{16}$H$_{15}$N$_2$OF$_5$—HCl requires C, 50.21; H, 4.21; N, 7.32. Found C, 50.20; H, 3.99; N, 7.22.

Example 3

1-azatricyclo[3.3.1.1$^{3,7}$]decan-4-one O-(4-chlorophenyl)oxime

Example 3A

N-(4-Chlorophenoxy)phthalimide:

Pyridine (0.37 mL, 4.6 mmol) was added to a suspension of N-hydroxyphthalimide (664 mg, 4.1 mmol), 4-chlorophenylboronic acid (635 mg, 4.1 mmol), and powdered 4 Å molecular sieves (1.02 g) in CH$_2$Cl$_2$ (20 mL). Cupric acetate monohydrate (812 mg, 4.1 mmol) was added, and the mixture was stirred open to the atmosphere at room temperature for 18 hours. Silica gel (10 g) was added, and the slurry was concentrated to dryness under vacuum. The residue was applied to the top of a flash chromatography column, and eluted with hexanes:ethyl acetate (80:20) to provide the title compound. $^1$H NMR (300 MHz, CDCl$_3$) δ 7.11-7.17 (m, 2 H), 7.27-7.34 (m, 2 H), 7.79-7.87 (m, 2 H), 7.88-7.95 ppm (m, 2 H).

Example 3B

O-(4-chlorophenyl)hydroxylamine

Hydrazine hydrate (0.56 mL, 12 mmol) was added to a solution of Example 3A (820 mg, 3.0 mmol) in chloroform (37 mL) and methanol (4 mL). The suspension was stirred at room temperature for 22 hours. Silica gel (10 g) was added, and the mixture was concentrated to dryness. The residue was applied to the top of a flash chromatography column and eluted with hexanes-ethyl acetate (80:20) to provide the title compound as the free amine. The residue was dissolved in ethanol (5 mL) and treated with HCl/dioxane (4M, 1 mL). The solution was heated at reflux and diluted with gradual addition of ethyl acetate (50 mL). The mixture was cooled to room temperature and filtered to provide the title compound as a hydrochloride salt. $^1$H NMR (300 MHz, CD$_3$OD) δ 7.15-7.22 (m, 2 H), 7.42-7.49 (m, 2 H).

Example 3C 1-azatricyclo[3.3.1.1$^{3,7}$]decan-4-one O-(4-chlorophenyl)oxime Example 3B (63 mg, 0.35 mmol) was added to a warm solution of 1-azatricyclo[3.3.1.1$^{3,7}$]decan-4-one (53 mg, 0.35 mmol) (prepared as reported in: Becker, D. P. and Flynn, D. L. Synthesis 1992, 1080-1082) in ethanol (2 mL). The mixture swirled with warming to dissolve all solids. The solution was allowed to stand at room temperature overnight, and crystallization was initiated by scratching with a glass rod. The resulting suspension was heated to dissolve the solids, and allowed to cool gradually to 0° C. to complete precipitation. The resulting solid was isolated by filtration and recrystallized from ethanol (1 mL) to provide the title compound as a hydrochloride salt. $^1$H NMR (300 MHz, CD$_3$OD) δ 2.13 (t, J=13 Hz, 2 H), 2.30-2.47 (m, 3 H), 3.06 (s, 1 H), 3.57-3.87 (m, 6 H), 4.00 (s, 1 H), 7.12-7.21 (m, 2 H), 7.25-7.34 ppm (m, 2 H); MS (DCI/NH$_3$) m/z 277/279 (M+H)$^+$; Anal. C$_{15}$H$_{17}$N$_2$OCl HCl requires C, 57.52; H, 5.79; N, 8.94. Found C, 57.24; H, 5.82; N, 8.62.

Example 4

1-azatricyclo[3.3.1.1$^{3,7}$]decan-4-one O-(6-chloropyridin-3-yl)oxime

Example 4A

2-[(6-chloropyridin-3-yl)oxy]-1H-isoindole-1,3(2H)-dione

The title compound was prepared as described in Example 3A, substituting 6-chloropyridin-3-ylboronic acid for 4-chlorophenyboronic acid.

Example 4B

O-(6-chloropyridin-3-yl)hydroxylamine

The title compound was prepared as described in Example 3B, substituting Example 4A for Example 3A. $^1$H NMR (300 MHz, CDCl$_3$) δ 7.22 (d, J=8 Hz, 1 H), 7.48 (dd, J=9, 3 Hz, 1 H), 8.26 ppm (d, J=3 Hz, 1 H).

Example 4C 1-azatricyclo[3.3.1.1³,⁷]decan-4-one O-(6-chloropyridin-3-yl)oxime A solution of 1-azatricyclo[3.3.1.1³,⁷]decan-4-one (120 mg, 0.80 mmol) (prepared as reported in: Becker, D. P. and Flynn, D. L. *Synthesis* 1992, 1080-1082) in ethanol (3.6 mL) was added to Example 4B (152 mg, 0.84 mmol). Concentrated HCl (12 M, 0.2 mL) was added, and the solution was heated at reflux for 5 minutes, and allowed to stand at room temperature for 60 hours. The solution was concentrated under vacuum and the residue was purified by chromatography (silica gel, eluted with $CH_2Cl_2$-$CH_3OH$—$NH_4OH$, 90:10:1). The free amine (70 mg) was dissolved in warm ethyl acetate (3 mL) and a solution of p-toluenesulfonic acid monohydrate (46 mg, 024 mmol) in warm ethyl acetate (1 mL) was added. The solution was heated to reflux, then allowed to cool gradually to −10° C. and kept at that temperature overnight. The solid was collected by filtration and dried under vacuum to provide the title compound as a p-toluenesulfonate salt: $^1$H NMR (300 MHz, $CD_3OD$) δ 2.07-2.21 (m, 2 H), 2.33-2.47 (m, 3 H), 2.36 (s, 3 H), 3.05-3.10 (m, 1 H), 3.62-3.74 (m, 4 H), 3.75-3.88 (m, 2 H), 4.01 (s, 1 H), 7.23 (d, J=8 Hz, 2 H), 7.41 (d, J=9 Hz, 1 H), 7.65-7.73 (m, 3 H), 8.29 ppm (d, J=3 Hz, 1 H); MS (DCI/$NH_3$) m/z 278/280 (M+H)⁺.

Example 5

N'-1-azatricyclo[3.3.1.1³,⁷]dec-4-ylidene-1H-indole-3-carbohydrazide

Example 5A

1H-Indole-3-carboxylic acid hydrazide

Indole-3-carboxylic acid (500 mg, 3.1 mmol) was stirred at room temperature with thionyl chloride (5 mL, 68 mmol) for 20 hours. The solution was concentrated under vacuum and the residue was taken up in ether (10 mL) and concentrated to dryness (repeated three times) to ensure removal of the thionyl chloride. The resulting solid was dissolved in ether (5 mL) and added to an ice cooled solution of hydrazine hydrate (600 mg, 12 mmol) in tetrahydrofuran (5 mL). After 30 minutes, the solid was collected by filtration, washed with 5% NaOH and water, and dried under vacuum at 50° C. The crude hydrazide was recrystallized from 95% ethanol to provide the title compound. $^1$H NMR (300 MHz, $CD_3OD$) δ 7.11-7.22 (m, 2 H), 7.42 (dd, J=7, 2 Hz, 1 H), 7.83 (s, 1 H), 8.02-8.08 ppm (m, 1 H); MS (DCI/$NH_3$) m/z 176 (M+H)⁺.

Example 5B

N'-1-azatricyclo[3.3.1.1³,⁷]dec-4-ylidene-1H-indole-3-carbohydrazide

A mixture of 1-azatricyclo[3.3.1.1³,⁷]decan-4-one (65 mg, 0.43 mmol) (prepared as reported in Becker, D. P. and Flynn, D. L. *Synthesis* 1992, 1080-1082) and Example 5A (80 mg, 0.46 mmol) were combined in a test tube with ethanol (7 mL). Concentrated hydrochloric acid (12 M, 0.04 mL) was added, and the mixture was heated at reflux until the solids dissolved. The solution was allowed to stand at room temperature overnight, then concentrated under vacuum. The residue was triturated with 10% ethanol in ethyl acetate (7 mL) and filtered to provide the title compound as the hydrochloride salt. $^1$H NMR (300 MHz, $CD_3OD$) δ 1.94 (d, J=13 Hz, 2H), 2.08 (br. s, 3H), 2.26 (d, J=12 Hz, 2H), 3.38-3.58 (m, 4H), 3.69 (d, J=12 Hz, 2H), 7.16-7.28 (m, 2H), 7.46 (dd, J=6, 1 Hz, 1H), 7.93-7.98 (d, J=3 Hz, 1H), 8.09 ppm (dd, J=6, 2 Hz, 1H); MS (DCI/$NH_3$) m/z 309 (M+H)⁺.

Example 6

1-azatricyclo[3.3.1.1³,⁷]decan-4-one O-benzyloxime

A mixture of 1-azatricyclo[3.3.1.1³,⁷]decan-4-one (45 mg, 0.30 mmol) (prepared as reported in Becker, D. P. and Flynn, D. L. *Synthesis* 1992, 1080-1082) and O-benzylhydroxylamine hydrochloride (Aldrich, 51 mg, 0.32 mmol) were combined in a test tube with ethanol (3 mL). Concentrated hydrochloric acid (12 M, 0.1 mL) was added, and the mixture was heated at reflux until the solids dissolved. The solution was allowed to stand at room temperature overnight, then concentrated under vacuum. The residue was dissolved in acetonitrile (0.7 mL), and the solution was diluted with ethyl acetate (5 mL). The resulting white precipitate was collected by filtration, washed with ethyl acetate (2 mL) and dried under vacuum to provide the title compound as the hydrochloride salt. $^1$H NMR (300 MHz, $CD_3OD$) δ 1.89-2.07 (m, 2 H), 2.15-2.37 (m, 3 H), 2.85 (s, 1 H), 3.42-3.85 (m, 7 H), 5.08 (s, 2 H), 7.24-7.40 ppm (m, 5 H); MS (DCI/$NH_3$) m/z 257 (M+H)⁺; Anal. $C_{16}H_{20}N_2O$·2HCl requires C, 58.36; H, 6.73; N, 8.51; Found C, 58.61; H, 6.49; N, 8.48.

Determination of Biological Activity

To determine the effectiveness of representative compounds of this invention as ligands for α7 NNRs, the compounds of the invention were evaluated according to the [$^3$H]-DPPB binding assay. To determine the effectiveness of representative compounds of this invention as ligands for α4β2 NNRs, the compounds of the invention were evaluated according to the [$^3$H]-cytisine binding assay, which were performed as described below.

[$^3$H]-Cytisine Binding

Binding to α4β2 NNRs subtype was determined according to the conditions which were modified from the procedures described in Pabreza L. A., Dhawan, S., Kellar K. J., [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM $CaCl_2$/2 mM $MgCl_2$/50 mM Tris-Cl, pH 7.4, 4° C.). Samples containing 100-200 μg of protein and 0.75 nM [$^3$H]-cytisine (30 $C_i$/mmol; Perkin Elmer/NEN Life Science Products, Boston, Mass.) were incubated in a final volume of 500 μL for 75 minutes at 4° C. Seven log-dilution concentrations of each compound were tested in duplicate. Non-specific binding was determined in the presence of 10 μM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM $CaCl_2$/2 mM $MgCl_2$). Packard MicroScint-20® scintillation cocktail (40 μL) was added to each well and radioactivity determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/(1+[Ligand]/K_D)$.

[$^3$H]-DPPB Binding

[$^3$H]-DPPB, [$^3$H]-(S,S)-2,2-dimethyl-5-(6-phenyl-pyridazin-3-yl)-5-aza-2-azonia-bicyclo[2.2.1]heptane iodide, binding to the α7 NNR subtype was determined using membrane enriched fractions from rat brain minus cerebellum or human cortex (ABS Inc., Wilmington, Del.) as described in Anderson, D. J.; Bunnelle, W.; Surber, B.; Du, J.; Surowy, C.; Tribollet, E.; Marguerat, A.; Bertrand, D.; Gopalakrishnan, M. J. Pharmacol. Exp. Ther. (2008), 324, 179-187 which is incorporated herein by reference. Briefly, pellets were thawed at 4° C., washed and resuspended with a Polytron at a setting of 7 in 30 volumes of BSS-Tris buffer (120 mM NaCl, 5 mM KCl, 2 mM $CaCl_2$, 2 mM $MgCl_2$, and 50 mM Tris-Cl, pH 7.4, 4° C.). Seven log-dilution concentrations of test compounds containing 100-200 μg of protein, and 0.5 nM [$^3$H]-DPPB (62.8 $C_i$/mmol; R46V, Abbott Labs) were incubated in a final volume of 500 μL for 75 minutes at 4° C. in duplicate. Non-specific binding was determined in the presence of 10 μM methyllycaconitine. Bound radioactivity was collected on Millipore MultiScreen® harvest plates FB presoaked with 0.3% polyethyleneimine using a Packard cell harvester, washed with 2.5 mL ice-cold buffer, and radioactivity was determined using a Packard TopCount Microplate beta counter. $IC_{50}$ values were determined by nonlinear regression in Microsoft® Excel or Assay Explorer. $K_i$ values were calculated from the $IC_{50}$s using the Cheng-Prusoff equation, where $K_i=IC_{50}/(I+[Ligand]/K_D)$. [$^3$H]-DPPB was obtained according to the preparation procedures described below.
[Methyl-3H]2,2-Dimethyl-5-(6-phenyl-pyridazin-3-yl)-5-aza-2-azonia-bicyclo[2.2.1]heptane iodide Preparation

[Methyl-3H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.
Step 1: Preparation of t-Butyl (S,S)-5-(6-Phenyl-pyridazin-3-yl)-2,5-diaza-bicyclo[2.2.1]heptane-2-carboxylate Triethylamine (20 mL) was added to a suspension of t-butyl (S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound. The filtrate was concentrated and the residue was purified by column chromatography on silica gel, eluting with ethyl acetate, to provide additional product: MS (DCI/$NH_3$) m/z 353 (M+H)$^+$.
Step 2: Preparation of (S,S)-2-Methyl 5-(6-phenyl-pyridazin-3-yl)-2,5-diaza-bicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 hour, and the brown solution was cooled to room temperature and concentrated under vacuum. The residue was purified by column chromatography on silica gel, eluting with $CH_2Cl_2$—$CH_3OH$—$NH_4OH$ (95:5:1) to provide the title compound: MS (DCI/$NH_3$) m/z 267 (M+H)$^+$.
Step 3: Preparation of [$^3$H]-(S,S)-2,2-Dimethyl-5-(6-phenyl-pyridazin-3-yl)-5-aza-2-azonia-bicyclo[2.2.1]heptane iodide ([$^3$H]-DPPB)

[$^3$H]Methyl iodide in toluene (250 mCi in 0.1 mL, 85Ci/mmol, American Radiolabeled Chemicals, Inc.) was combined with a solution of the product obtained from Step 2 in dichloromethane (0.788 mg, 2.96 μmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 mL acetonitrile:water:trifluoroacetic acid (15:85:0.1). Approximately 0.9 mL per injection were made onto a Phenomenex® Luna® C18(2) column (5 micron, 250 mm×4.6 mm ID) using an Agilent HPLC system. [$^3$H]-DPPB was eluted by a gradient mobile phase from 10% B to 20% B in 20 minutes where Mobile Phase A=0.1% trifluoroacetic acid in water and Mobile Phase B=0.1% trifluoroacetic acid in acetonitrile at a flow rate of approximately 1 mL/minute. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.
Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 μL flow cell and a 3:1 ratio of Ultima-Flo M scintillation cocktail to HPLC mobile phase were used. The analyses were performed using a Phenomenex® Luna® C18(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/minute and the UV detection was set at 275 nm.

Compounds of the invention typically exhibited binding values ($K_i$) below 10 micromolar in one or both of these assays ([$^3$H]-Cytisine or [$^3$H]-DPPB binding). Preferred compounds had Ki values ranging from 0.01 nanomolar to 100 nanomolar in one or both binding assays.

Compounds of the invention are ligands at α4β2, α7 NNRs, or both α4β2 and α7 NNRs that modulate function of α4β2, α7 NNRs, or both α4β2 and α7 NNRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α4β2, α7, or both α4β2 and α7 NNR receptor or agonists that activate the receptor. Binding to α4β2, α7, or both α4β2 and α7 receptors also trigger key signaling processes involving various kinases and phosphatases and protein-protein interactions that are important to effects on memory, cytoprotection, gene transcription and disease modification.

Compounds of the invention can exist in radiolabeled form containing one or more atoms having an atomic mass or mass number different from the atomic mass or mass number most abundantly found in nature. Radioisotopes of atoms such as hydrogen, carbon, phosphorous, sulfur, fluorine, chlorine and iodine include, but are not limited to, $^3$H, $^{14}$C, $^{32}$P, $^{35}$S, $^{18}$F, $^{36}$Cl, and $^{125}$I, respectively. Compounds that contain other radioisotopes of these and/or other atoms are within the scope of this invention. Compounds containing tritium ($^3$H) and $^{14}$C radioisotopes are preferred an general for their ease in preparation and detectability. Radiolabeled compounds of this invention can be prepared by the general methods well known to persons having ordinary skill in the art. Such radiolabeled compounds can be conveniently prepared by carrying out the procedures disclosed in the above Examples and Schemes by substituting a readily available radiolabeled reagent for a non-radiolabeled reagent. The radiolabeled compounds of the invention can be used as standards to determine the effectiveness of α7 NNR ligands in binding assays such as the assays described above.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

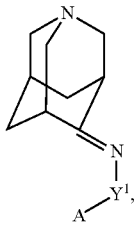

wherein $Y^1$ is a bond, —N($R^x$)—C(O)—, —O—, —N($R^x$)—C(O)—N($R^y$)—, —O—C(O)—, or —N($R^z$)—;

A is aryl, heteroaryl, arylalkyl, or heteroarylalkyl wherein the aryl, heteroaryl, the aryl moiety of arylalkyl, and the heteroaryl moiety of the heteroarylalkyl are each independently unsubstituted or substituted; and $R^x$, $R^y$, and $R^z$, at each occurrence, are each independently hydrogen, alkyl, or haloalkyl;

or a pharmaceutically acceptable salt or amide thereof.

2. The compound according to claim 1, wherein $Y^1$ is —N($R^x$)—C(O)— or —O—C(O)—, wherein $Y^1$ is attached to A of formula (I) through —C(O)— moiety, or a pharmaceutically acceptable salt or amide thereof.

3. The compound according to claim 1 wherein $Y^1$ is —N($R^x$)—C(O)— and A is aryl or heteroaryl, or a pharmaceutically acceptable salt or amide thereof.

4. The compound according to claim 1 wherein $Y^1$ is —N($R^x$)—C(O)— and A is arylalkyl or heteroarylalkyl, or a pharmaceutically acceptable salt or amide thereof.

5. The compound according to claim 1 wherein $Y^1$ is —O—, or a pharmaceutically acceptable salt or amide thereof.

6. The compound according to claim 1 wherein $Y^1$ is —O— and A is aryl or heteroaryl, or a pharmaceutically acceptable salt or amide thereof.

7. The compound according to claim 1 wherein $Y^1$ is —O— and A is arylalkyl or heteroarylalkyl, or a pharmaceutically acceptable salt or amide thereof.

8. The compound according to claim 1 selected from the group consisting of
1-azatricyclo[3.3.1.1$^{3,7}$]decan-4-one O-2-naphthyloxime;
1-azatricyclo[3.3.1.1$^{3,7}$]decan-4-one O-(pentafluorobenzyl)oxime;
1-azatricyclo[3.3.1.1$^{3,7}$]decan-4-one O-(4-chlorophenyl)oxime;
1-azatricyclo[3.3.1.1$^{3,7}$]decan-4-one O-(6-chloropyridin-3-yl)oxime;
N'-1-azatricyclo[3.3.1.1$^{3,7}$]dec-4-ylidene-1H-indole-3-carbohydrazide; and
1-azatricyclo[3.3.1.1$^{3,7}$]decan-4-one O-benzyloxime;
or a pharmaceutically acceptable salt or amide thereof.

9. A pharmaceutical composition comprising a therapeutically effective amount of the compound of claim 1, or a pharmaceutically acceptable salt or amide thereof, in combination with one or more pharmaceutically acceptable carriers.

10. The pharmaceutical composition of claim 9 further comprising one or more atypical antipsychotics.

* * * * *